United States Patent [19]
Fukuchi

[11] Patent Number: 4,983,822
[45] Date of Patent: Jan. 8, 1991

[54] VARIABLE OPTICAL AXIS TYPE BOTTLE INSPECTING APPARATUS

[75] Inventor: Hiroyuki Fukuchi, Yokohama, Japan

[73] Assignee: Kirin Beer Kabushiki Kaisha, Tokyo, Japan

[21] Appl. No.: 357,287

[22] Filed: May 26, 1989

[30] Foreign Application Priority Data

May 27, 1988 [JP] Japan .................................. 63-128246

[51] Int. Cl.$^5$ .......................... G01N 9/04; G01N 21/00
[52] U.S. Cl. .................................. 250/223 B; 356/240
[58] Field of Search ............... 250/223 B, 223 R, 228, 250/234, 235; 356/240; 358/106; 209/522, 524, 526, 529

[56] References Cited

U.S. PATENT DOCUMENTS

| | | | |
|---|---|---|---|
| 3,411,009 | 11/1968 | Ford et al. | 250/223 B |
| 3,797,632 | 3/1974 | Riggs | 250/223 B |
| 4,241,256 | 12/1980 | Tagaya et al. | 250/223 B |
| 4,376,951 | 3/1983 | Mirazawa | 356/240 |
| 4,509,081 | 4/1985 | Peyton et al. | 250/223 B |

Primary Examiner—David C. Nelms
Assistant Examiner—Michael Messinger
Attorney, Agent, or Firm—Fleit, Jacobson, Cohn, Price, Holman & Stern

[57] ABSTRACT

A variable optical axis type bottle inspecting apparatus is disclosed. The bottle inspecting apparatus comprises illuminating means for illuminating a bottle continuously conveyed on rotation, an optical system for forming an image of lights transmitted through the bottle, photoelectric converting means for photoelectrically converting the transmitted light image of the bottle, optical axis changing means for changing the optical axis of the optical system with respect to the photoelectric converting means so that the transmitted light image of the bottle continuously conveyed is formed consecutively on the photoelectric converting means, and inspecting means for inspecting the sidewall of the bottle for defects, based on the transmitted light images photoelectrically converted by the photoelectric converting means. In the variable optical axis type bottle inspecting apparatus, the optical axis of an optical system is varied relatively to photoelectric means, whereby images of lights transmitted through a bottle on continuous move are formed consecutively on photoelectric means. This makes it possible that a bottle on continuous move is followed with the optical path not bent orthogonal. Consequently the apparatus can be miniaturized as a whole.

12 Claims, 6 Drawing Sheets

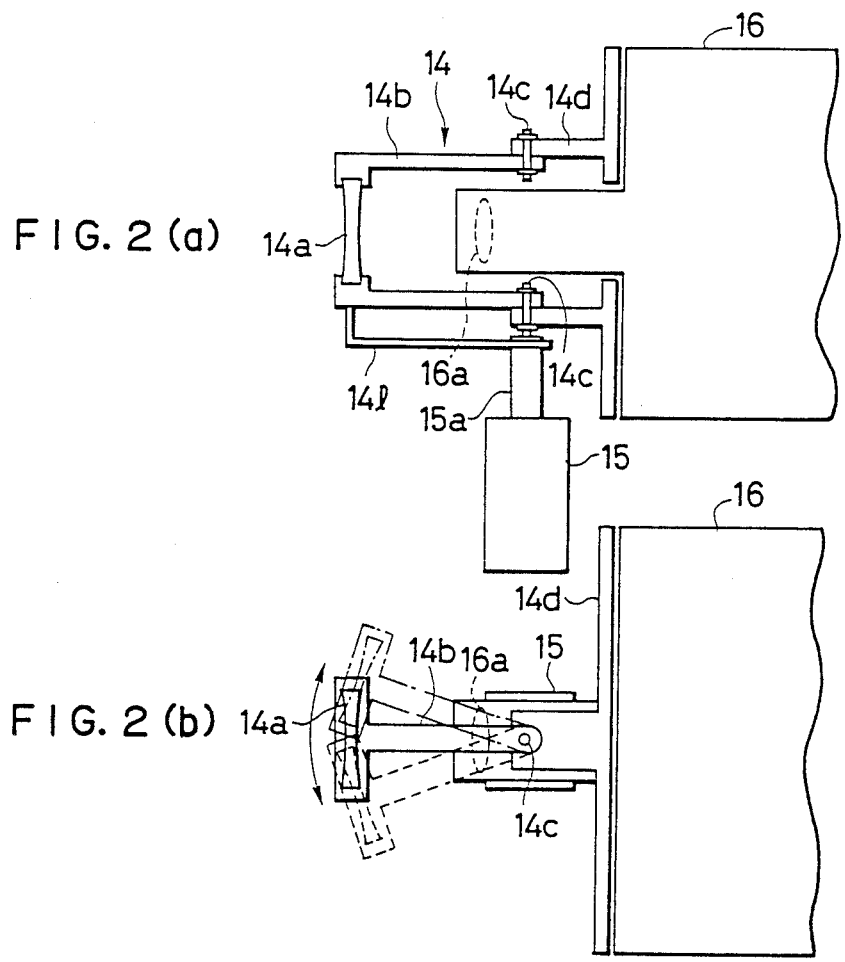
FIG. 2(a)
FIG. 2(b)
FIG. 3
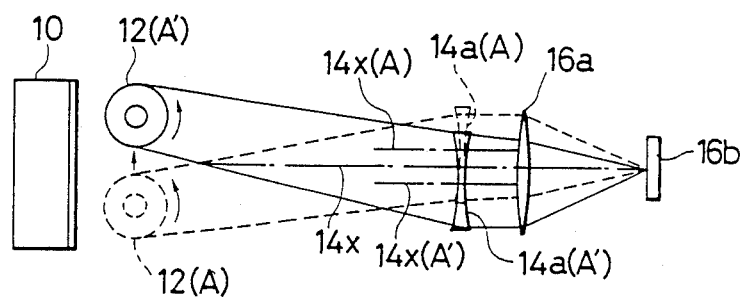

VARIABLE OPTICAL AXIS TYPE BOTTLE INSPECTING APPARATUS

BACKGROUND OF THE INVENTION

This invention relates to a variable optical axis type bottle inspecting apparatus for detecting defects on a bottle on rotation.

Glass bottles containing liquors, beverages, foods, etc. have to be inspected for any defect whether the bottles are newly made or have been recovered for reuses. The bottles are inspected on portions, i.e., the body or sidewall, bottom, top of the mouth, and threaded bottle neck. A bottle being inspected is conveyed continuously at a high speed while being rotated. Conventionally a mirror is inserted in an optical path and is moved so as to enable a camera to follow the bottle on continuous move.

But a problem with the bottle inspecting apparatus including the mirror is that the optical path is bent substantially orthogonal which makes the apparatus large-sized.

SUMMARY OF THE INVENTION

An object of this invention is to provide a compact bottle inspecting apparatus with the optical path not bent, which is capable of following a bottle on continuous move.

This object is achieved by a variable optical axis type bottle inspecting apparatus comprising: illuminating means for illuminating a bottle continuously conveyed on rotation; an optical system for forming an image of lights transmitted through the bottle; photoelectric converting means for photoelectrically converting the transmitted light image of the bottle; optical axis changing means for changing the optical axis of the optical system with respect to the photoelectric converting means so that the transmitted light image of the bottle continuously conveyed is formed consecutively on the photoelectric converting means; and inspecting means for inspecting the sidewall of the bottle for defects, based on the transmitted light images photoelectrically converted by the photoelectric converting means.

In the variable optical axis type bottle inspecting apparatus according to this invention, the optical axis of an optical system is varied relatively to photoelectric means, Whereby images of lights transmitted through a bottle on continuous move are formed consecutively on photoelectric means. This makes it possible that a bottle on continuous move is followed with the optical path not bent orthogonal. Consequently the apparatus can be miniaturized as a whole.

BRIEF DESCRIPTION OF THE DRAWINGS

FIGS. 2a, 2b, and 3 are views of optical systems used in the variable optical axis type bottle inspecting apparatus of FIG. 1

DETAILED DESCRIPTION OF THE INVENTION

Figure 1:
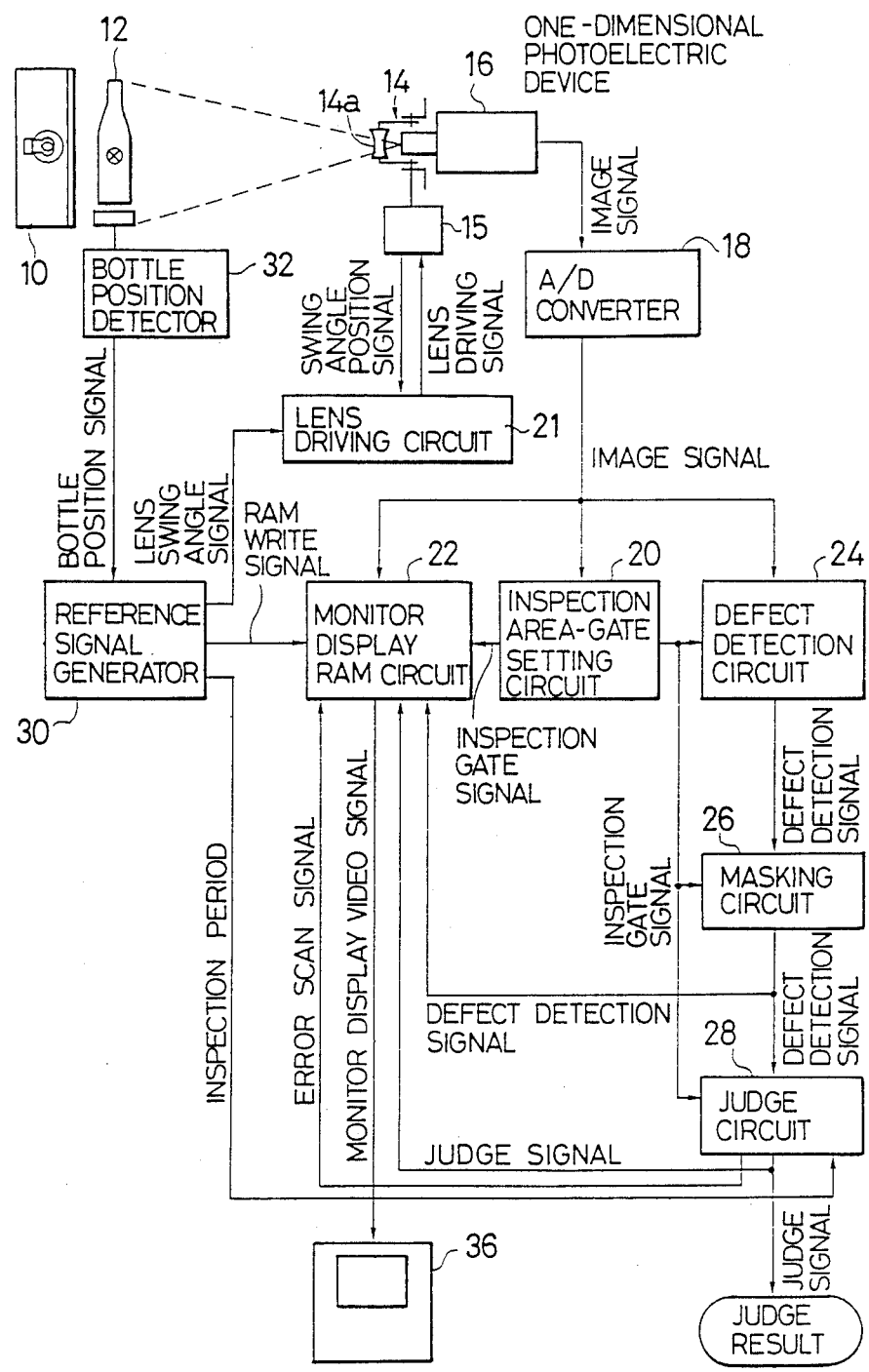
FIG. 1 is a block diagram of the variable optical axis type bottle inspecting apparatus according to one embodiment of this invention.

FIG. shows the variable optical axis type bottle inspecting apparatus according to one embodiment of this invention. A bottle 12 to be inspected by the apparatus according to this invention is conveyed continuously while being rotated. The bottle 12 is illuminated by a diffused light source 10 with a surface for emitting uniform diffused lights. An image of lights transmitted through the sidewall of the bottle 12 (a transmitted light image) is formed on a one-dimensional photoelectric device 16 by way of an optical axis changing unit 14. The one-dimensional photoelectric device 16 comprises a photo detecting unit for converting a transmitted light image to an electric analog signal as a linear CCD does, and an optical system for forming a transmitted light image of the sidewall of a bottle.

The optical axis changing unit 14 is disposed on the side of the optical system of the one-dimensional photoelectric device 16 opposed to the bottle 12 and changes the optical axis of the optical system relative to the photo detecting unit of the one-dimensional photoelectric device 16. The optical axis changing unit 14 changes the optical axis synchronously with movement of the bottle 12 so that a transmitted light image may be formed on the photo detecting unit of the one-dimensional photoelectric device 16. That is, for a change of the optical axis, a lens 14a provided on the front of the one-dimensional photoelectric device 16 is driven by a motor 15 driven by a lens driving circuit 21.

The one-dimensional photoelectric device 16 and the optical axis changing unit 14 are shown in more detail in FIG. 2. FIG. 2(a) is a side view, and FIG. 2(b) is a plan view. The optical system for forming a transmitted light image of the bottle 12 comprises a combination lens 16a provided on the forward end of the one-dimensional photoelectric device 16, and a concave lens 14a in the optical axis changing unit 14. The optical axis changing unit 14 swings the concave lens 14a so as to change the optical axis. A lens support member 14b has one end supporting the concave lens 14a and the other end connected to a support member 14d swingably on a pin 14c. The support member 14d is fixed to the front of the one dimensional photoelectric device 16 The drive shaft 15a of the motor 15, and the forward end of the lens support member 14b are interconnected by an arm 14e so that, as shown in FIG. 2(b), the concave accordance with clockwise and counter-clockwise rotation of the motor shaft 15a by a certain angle.

The principle of following the bottle 12 continuously moving on rotation will be explained with reference to FIG. 8. The optical axis changing unit 14 changes the optical axis of the optical system with respect to the linear CCD 16b, and with respect to the bottle 12 on continuous move the optical axis changing unit 14 changes the optical axis 14x of the concave lens 14a as shown in FIG. 3. That is, as the bottle 12 is conveyed from a position A to a position A', the concave lens 14 is moved from the position A' to the position A in the opposite direction of conveyance of the bottle 12, so that the optical axis 14x is changed from the position A to the position A'. This arrangement permits the center of a transmitted light image of the bottle 12 to be formed constantly at a given position of the rotation during the conveyance from the position A to the position A'. Resultantly an image of the entire circumference of the bottle 12 can be inputted by means of the linear CCD.

An A/D converter is converts an analog image signal from the one-dimensional photoelectric converter 16 into a digital image signal of a given bit number. The digital image signal is supplied to an inspection area gate setting circuit 20, a monitor display RAM circuit 22 and a defect detection circuit 24.

Figure 4:
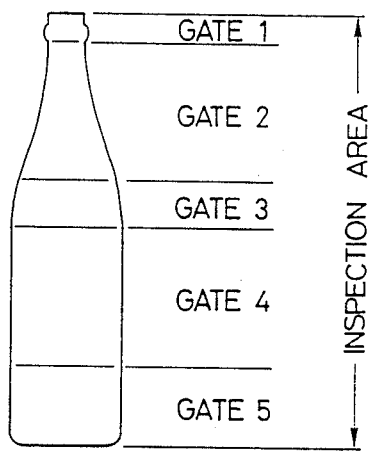
FIG. 4 is a view showing inspection areas and inspection gates of the variable optical axis type bottle inspecting apparatus of FIG. 1.

As shown in FIG. 4, the inspection area gate setting circuit 20 determines vertically sectioned inspection areas of a transmitted light image where the defect detection circuit 24 detects defects based on the transmitted light image which will be explained below. The inspection areas may be determined based on the upper and the lower end edges of the bottle 12 depending on a shape of the bottle 12, or may be fixed. In FIG. 4, the inspection area is set on the entire bottle, and the inspection area is divided into inspection gates 1, 2, 3, 4, and 5 in accordance with the shape of the bottle 12. The inspection area gate setting circuit 20 supplies an inspection gate signal indicative of an inspection gate of the inspection area in which is a current scan position of the linear CCD 16b to the monitor display RAM circuit 22, the defect detection circuit 24, a masking circuit 26, and a judge circuit 28.

Based on a digital image signal from the A/D converter 18, the defect detection circuit 24 compares in brightness a plurality of points spaced vertically and horizontally from each other by a given distance so as to detect defects.

The defect detecting method includes a two-point defect detecting system, in which brightness is compared between two points, and a three-point defect detecting system in which brightness is compared among three points. FIG. 5 explains the two-point defect detecting system, and FIG. 6 explains the three-point defect detecting system.

In the two point defect detecting system, when the following formula $$| QA - QB | \geq (\text{constant A})$$

in which brightnesses at two points A and B are represented by QA and QB respectively is satisfied, there are defects.

Figure 5A:
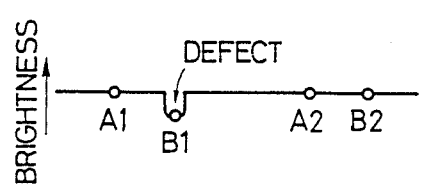
FIGS. 5a, 5b, 6a and 6b are explanatory views of defect detecting systems of the variable optical axis type bottle inspecting apparatus of FIG. 1.
Figure 6A:
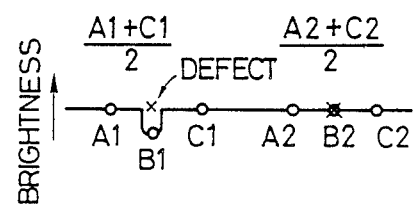
Figure 5B:
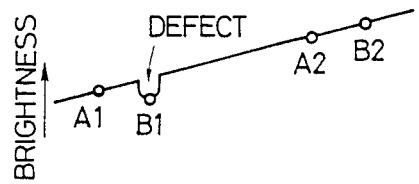

In the case of FIG. 5, defects can be detected by the following formula $$| QA1 - QB1 | \geq (\text{constant A})$$

$$| QA2 - QB2 | \geq (\text{constant A})$$

in which brightnesses at points A1 and B1, and A2 and B2 on one scanning line are represented respectively by QA1, QB1, QA2, QB2. A constant A is preset in accordance with types, etc. of the bottle 12. As shown in FIG. 5(a), when a transmitted light image has even brightness along a scanning line, $$QA1 - QB1 > A$$

$$QA2 - QB2 = 0$$

are satisfied, and it is found that the point B1 is a defect. This two-point defect detecting system is effective for the case of even brightness. In the case of uneven brightness along a scanning line as shown in FIG. 5(b), the following formulas $$| QA1 - QB1 | < A$$

$$| QA2 - QB2 | < A$$

are given. There is a risk that the defect at the point B1 will be missed.

Figure 6B:
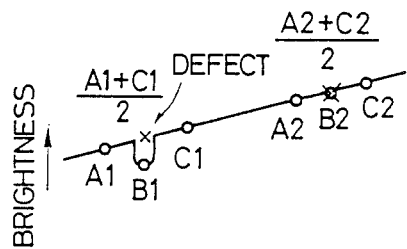

But the three-point defect detecting system enables defects to be detected without failure even in the case of uneven brightness along a scanning line as shown in FIG. 6(b). In the three-point defect detecting system, the following formula $$| QB - \{( QA + QC )/2\} | \geq (\text{constant B})$$

in which brightnesses at three points A, B, and C are represented by QA, QB and QC is used to detect defects. A constant B is preset in accordance with types, etc. of the bottle 12.

In the case of FIG. 6, defect are detected using the following formulas $$|QB1 - \{(QA1+QC1)/2\}| \geq (\text{constant B})$$

$$|QB2 - \{(QA2+QC2)/2\}| \geq (\text{constant B})$$

in which brightnesses at points A1, B1, C1 on a scanning line of the area CCD 16b are represented by QA1, QB1, QC1, QA2, QB2, QC2. The brightnesses compared With those at intermediate points 81 and 82 are an arithmetic average of the brighteners of points A1 and C1 on both sides of the intermediate point B1 and that of the brightnesses of points A2 and C2 on both sides of the intermediate point B2, respectively. The three-point defect detecting system enables the defect B1 to be detected correctly both in the case of even brightness as in FIG. 6(a) and in the case of uneven brightness as in FIG. 6(b).

Figure 7:
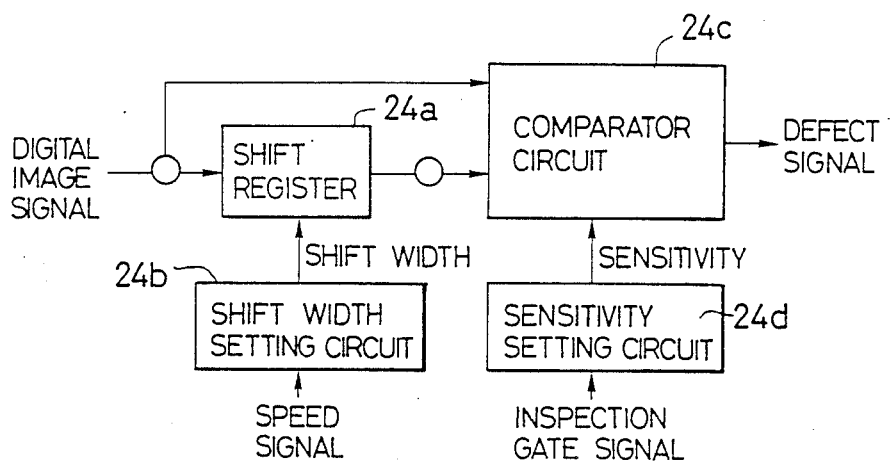
FIG. 7 is a block diagram of an example of the defect detecting circuit for conducting the defect detecting system of FIG. 5.

FIG. 7 shows an example of the defect detection circuit 24 for the two-point defect detecting system. A distance between two points is determined by a shift width of a shift register 24a to which is sequentially inputted a digital image signal. The shift width is determined by a shift width setting unit 24b. A comparator 24c compares a currently inputted digital image signal with an output signal of the shift register 24a which is a preceding signal by a shift width so as to judge whether or not the absolute value of a difference between the two is larger than a sensitivity (i e., a constant A) set by the sensitivity setting unit 4d. The constant A varies for the inspection gates. The sensitivity setting unit 24d outputs a suitable constant A based on an input inspection gate signal to the comparator 24c.

Figure 8:
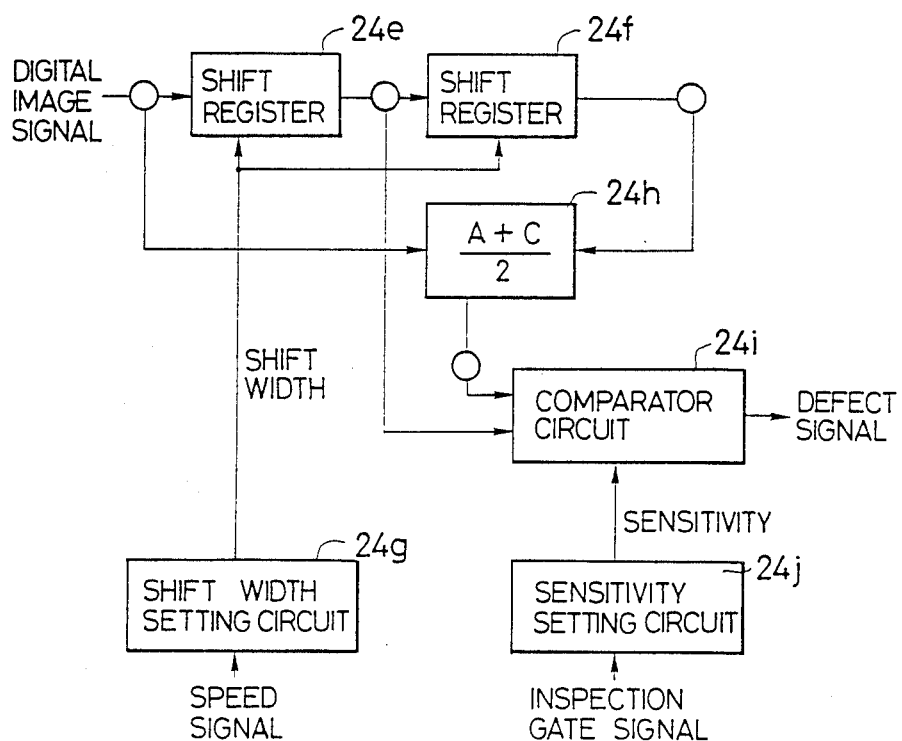
FIG. 8 is a block diagram of an example of the defect detecting circuit for conducting the defect detecting system if FIG. 6.

FIG. 8 shows an example of the defect detection circuit 24 of the three-point defect detecting system. The distance between one of the three points and an adjacent one is determined by shift widths of a shift registers 24e, 24f to which are sequentially supplied digital image signals. In this example, the two shift registers 24e, 24f have the same shift width. A computing circuit 24h computes an arithmetic average of a current input digital image signal and a digital image signal outputted from the shift register 24f. A comparator 24i compares an average brightness computed by the computing circuit 24h with a digital image signal from the shift register 24e to judge whether or not the absolute value of a difference between the two is larger than a sensitivity (i.e., a constant B) set by a sensitivity setting unit 24j to output a defect signal. The constant B varies for the inspection gates. The sensitivity settIng unit 24j outputs to the comparator 24i a suitable constant 8 based on an input inspection gate signal.

In the defect detecting circuits of Figs. 7 and 8 in which two points or three points on a scanning line of the linear CCD 16b (i.e., vertically of the bottle 12) are compared in brightness, when two or three points located horizontally of the bottle 12 are compared in brightness, digital image signals are stored in a memory (not shown) for a number of necessary scanning lines, and the digital image signals are sequentially read from the memory vertically of the scanning lines to input the read digital image signals in a shift register 24a or 24b. In this case, the digital image signal supplied to the shift register 24a or 24b depends on a spinning speed of the bottle 12, and thus a spinning speed signal is supplied to a shift width circuit 24b or 24g which sets shift widths. Consequently, even when the spinning speed varies, two or three points spaced from one another by a substantially constant distance can be compared.

A defect signal outputted from the defect detection circuit 24 is masked by a masking circuit 26. When the sensitivity of the defect detection circuit 24 is increased to avoid errors in the defect detection, a part which is not a defect is falsely detected as a defect. The masking is for removing such false defect signal. At a real defect, defect signals are continuously generated in accordance with a size of the defect, and at the remaining normal part, defect signals are separately generated. The masking eliminates as a false defect signal an isolated defect signal and defect signals continuing only below a set value.

A judge circuit 28 judges whether or not a defect is present, based on defect signals which have been masking. For example, a number of the defect signals are counted for each scan, and when the counted value exceeds a set value, the scan is judged an error scan (a defect scan line). The judge circuit 28 further counts a number of continuous error scans, and when the counter value exceed a set value, the bottle 12 is judged a defective bottle. A resultant judge signal is outputted to a conveying line (not shoWn), and in accordance with the judge signal, the conveying system ejects the defective bottle.

A reference signal generator 30 generates and outputs a lens swing angle signal, an inspection period signal and a RAM write signal, based on a bottle position signal from a bottle position detector 32. The lens sWing angle signal is for swinging the concave lens 14a so that an image on the center line of the bottle 12 is formed constantly on the one-dimensional photoelectric device 16 and is supplied to the lens driving circuit 21. The lens driving circuit 21 swings the concave lens 14a based on the lens swing angle signal. The inspection period signal is for indicating an inspection period in which the concave lens 14a moves following the bottle 12 on continuous move and is supplied to the judge circuit 28. The RAM write signal is for indicating a timing for a digital image signal to be written in the monitor display RAM unit 22. A monitor 36 displays a digital image signal of 480 scans at an equal pitch in an inspection period indicated by the inspection signal.

Figure 9:
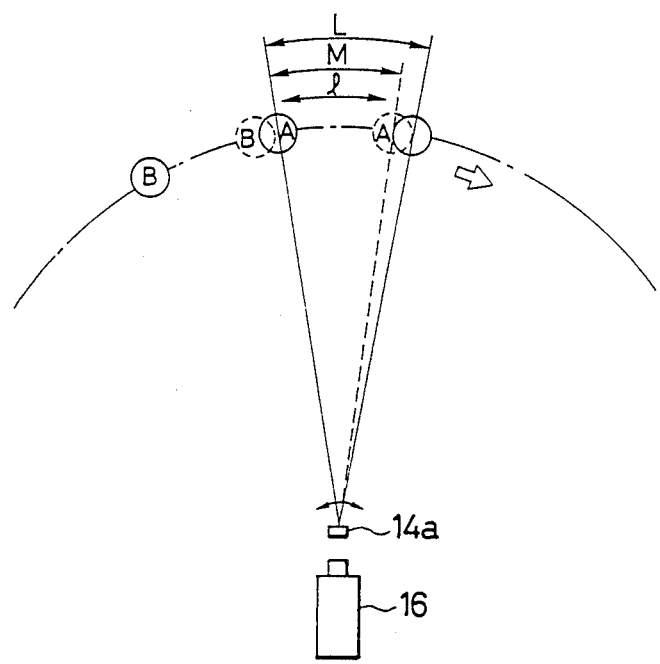
FIGS. 9 and 10 are views explaining the relationships of a bottle position with a lens swing angle signal, an inspection period signal and a RAM write signal for the variable optical axis type detecting apparatus of FIG. 1.
Figure 10:
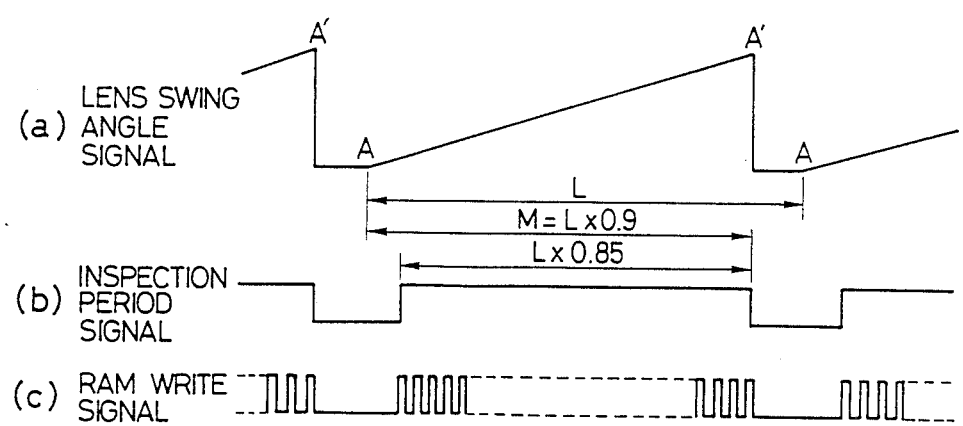

FIGS. 9 and 10 show the relationships among the lens swing angle, the inspection period signal, and the RAM write signal. As shown in FIG. 9, a pitch for the bottle 12 to be continuously conveyed at is represented by L: a distance for the bottle to travel over during one rotation, 1 ($=L\times0.8$); and a distance for the concave lens 14a to follow the bottle 12 over, M ($=L\times0.9$).

The lens swing angle is so changed that the concave lens 14a is swung in the direction opposite to the conveyance of the bottle 12 while the bottle 12 is between the points A and A' (FIG. 10(a)) and is so changed that the concave lens 14a is returned to the position A' as soon as the bottle 12 reaches the position A'. At this time a next bottle 12 is at a position B, and the lens swing angle signal is not changed until the next bottle 12 reaches the point A. When the next bottle 12 reaches the position A, the lens swing angle signal is so changed that the concave lens 14a follow the next bottle 12.

The inspection period signal is set so as to alloW the bottle 12 to make one rotation over the distance 1 while the concave lens 14a is following the bottle 12 over the distance M. That is, the inspection period signal becomes high level during a period corresponding to $L\times0.85$ ($>1$).

The RAM write signal is of pulses corresponding to a number of scanning lines necessary to scan the entire circumference of the bottle 12. For example, when a pulse signal corresponding to 480 scanning lines for scanning the entire circumference of the bottle 12 is written in the monitor display RAM unit 22, as shown in FIG. (d), a RAM write signal of 480 pulses is outputted at the high level of an inspection period signal.

The reference signal generator 30 uses a ROM for generating the lens swing angle signal, the inspection period signal and the RAM write signal. That is, a lens swing angle signal, an inspection period signal and a RAM signal are written beforehand in the ROM at an address of a bottle position signal. A bottle position signal is inputted as an address, and then a lens swing angle signal, an inspection period signal and a RAM write signal are supplied.

Based on a lens swing angle signal from the reference signal generator 30, the lens driving circuit 21 drives the concave lens 14a. The lens driving circuit 21 performs the feedback control using the lens swing angle signal as a feedback signal. Unless the concave lens 14a outputs a lens swing angle signal, the lens driving circuit 2i controls in the open-loop.

An inspection period signal from the reference signal generator 30 is supplied to the judge circuit 28. The judge circuit 28 judges whether or not the bottle 12 is defective by taking as effective the defect signals supplied thereto in a period when the inspection period signal is of high level. Otherwise it is possible to output an inspection period signal from the reference signal generator 30 to the inspection area gate setting circuit 20, the defect detection circuit 24, or the masking circuit 26 to take as effective only the defect detecting signals supplied in a period when the inspection period signal is of high level.

A RAM write signal from the reference signal generator 30 is outputted to the monitor display RAM circuit 22. Based on this RAM write signal, a digital image signal the A/D converter 18 is written in the monitor display RAM circuit 22. The monitor display RAM circuit 22 has been supplied, in addition to the RAM write signal, with a defect detecting signal from the masking circuit 26, an erroneous scan signal and a judge result signal from the judge circuit 28, and an inspection gate signal from the inspection area gate setting circuit 20. Based on the defect signal and the erroneous scan signal, defects and erroneous scans are written in the monitor display RAM circuit 22. Based on the inspection gate signal, an inspection gate is displayed on the monitor 36.

The monitor display RAM circuit 22 has two frame memories and alternately uses the two frame memories to store a digital image signal of the bottle 12 being inspected, and that of an immediately preceding inspected bottle 12. Normally the digital image signal of the bottle 12 being inspected is displayed continuously on the monitor 36, but when a judge signal indicative of a defective bottle is inputted from the judge circuit 28, the content of the digital image signal of the defective bottle stored in the frame memory is displayed on the monitor 36 for detailed inspection of the defective condition.

As described above, the apparatus according to this embodiment, which is compact, makes it possible to locate defects on the sidewall of a bottle continuously conveyed on rotation and inspect the same.

This invention is not limited to the above-described embodiment and cover various modifications.

In the embodiment, as shown in FIG. 2, the concave lens 14a is provided on the front of the one-dimensional photoelectric device 16 and swung, but in place of the concave lens, a convex lens may be used and swung.

Figure 11:
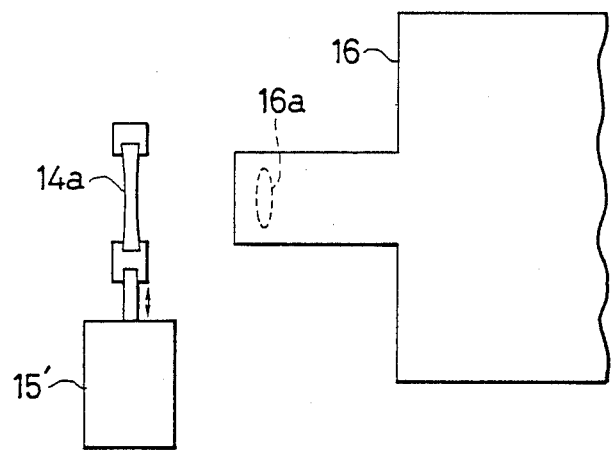
FIG. 11 is a view of another embodiment of the variable optical axis type bottle inspecting apparatus.

As shown in FIG. 11, the concave lens 14a may be driven linearly by linear drive means 15' so as to change the optical axis.

Figure 12:
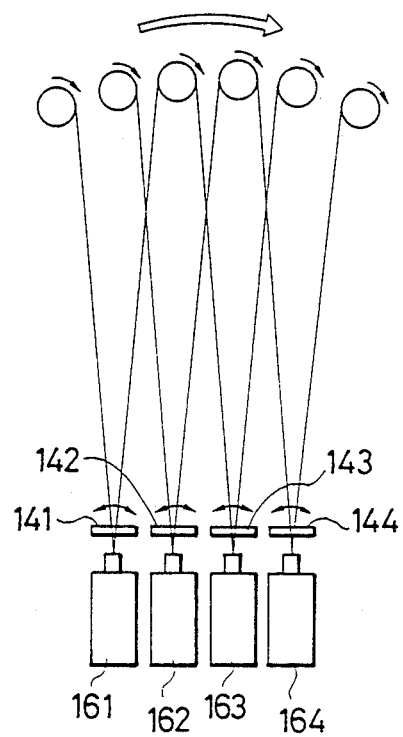
FIG. 12 is a view of further another embodiment of the variable optical axis type defect inspecting apparatus.

According to this invention, the lens and the one-dimensional photoelectric converter are arranged linearly to constitute the optical system. This allows the optical system to be adjacently arranged in a plural number. Even in the case the bottle 12 is conveyed continuously at such a high speed that it is impossible to inspect the bottle for defects by means of one optical system, as shown in FIG. 12, four optical systems respectively comprising concave lenses 141, 142, 143, 144, and one-dimensional photoelectric apparatus 161, 162, 163, 164 are arranged to enable the bottle 12 conveyed at such a high speed to be inspected for defects.

In the embodiment, the one-dimensional photoelectric device is used for the detection of a transmitted light image of the bottle 12, but a two-dimensional photoelectric device, such as an area CCD, may be used. In the case of using the two-dimensional photoelectric device, the optical axis changing unit changes &he optical axis, so that the bottle 12 continuously conveyed is followed, and the two-dimensional photoelectric device converts a transmitted light image at a preset timing. The use of the two-dimensional photoelectric device allows images of transmitted lights through one bottle at a plural positions thereof while the bottle is continuously conveyed. The inspection result becomes accordingly precise.

The defect detecting system used in this apparatus is not limited to the system described in the embodiment and may cover various modifications. To give examples, it is possible that when the following formulae $$QA / QB \geqq \text{(constant C)}$$

$$QA / QB \geqq 1/\text{(constant C)}$$

where brightnesses to be computed for comparison are denoted by QA and QB are satisfied, a defect is present. It is also possible that when the following formulae $$QB / \{(QA+QC)/2\} \geqq \text{(constant D)}$$

$$QB / \{(QA+QC)/2\} \geqq 1/\text{(constant D)}$$

where brightnesses at three points to be compared are represented by QA, QB and QC, and constants C and D are numbers 1 or more, a defect is present.

This invention can be applicable to any part other than the sidewall of a bottle. The principle of this invention is applicable to the inspection of objects other than bottles.

What is claimed is:

1. A variable optical axis type bottle inspecting apparatus comprising:

illuminating means for illuminating a bottle continuously conveyed in the direction of a conveying means and rotated about its axis by a rotating means;

an optical system for forming an image of lights transmitted through the bottle, the optical system having a lens for changing the optical axis of an optical system inserted in an optical path interconnecting a photoelectric converting means and the bottle being mounted independently of the rotating means for the bottle;

photoelectric converting means for photoelectrically converting the transmitted light images of the bottle;

optical axis changing means for moving the lens to change the optical axis of the optical system with respect to the photoelectric converting means in synchronization with the movement of the bottle so that the transmitted light images of the bottle continuously conveyed are detected continuously by the photoelectric converting means; and inspecting means for inspecting the sidewall of the bottle for defects, based on the transmitted light images photoelectrically converted by the photoelectric converting means.

2. A variable optical axis type defect inspecting apparatus according to claim 1, wherein he lens for changing the optical axis comprises a concave lens.

3. A variable optical axis type bottle inspecting apparatus according to claim 1, wherein the optical axis changing means has swing means for swinging the lens for changing the optical axis in synchronization with the movement of the bottle.

4. A variable optical axis type bottle inspecting apparatus according to claim 3, wherein the optical axis changing means has linear driving means for swinging the lens for changing the optical axis, in synchronization wi&h the movement of the bottle.

5. A variable optical axis type defect inspecting apparatus according to claim 1, wherein the lens for changing the optical axis comprises a convex lens.

6. A variable optical axis type defect inspecting apparatus according to claim 3, wherein the lens for changing &he optical axis comprises a convex lens.

7. A variable optical axis type defect inspecting apparatus according to claim 4, wherein the lens for changing the optical axis comprises a convex lens.

8. A variable optical axis type bottle inspecting apparatus according to claim 6, wherein the swing means comprises a drive motor having a drive shaft which oscillates through a predetermined angle, and a support member for supporting the lens to swing the lens in accordance with the oscillation of the drive shaft.

9. A variable optical axis type defect inspecting apparatus according to claim 3, wherein the lens for changing &he optical axis comprises a concave lens.

10. A variable optical axis type defect inspecting apparatus according to claim 4, wherein the lens for changing the optical axis comprises a concave lens.

11. A variable optical axis type bottle inspecting apparatus according to claim 3, wherein the swing means comprises a drive motor having a drive shaft which oscillates through a predetermined angle, and a support member for supporting the lens to swing the lens in accordance with the oscillation of the drive shaft.

12. A variable optical axis type bottle inspecting apparatus according to claim 9, wherein the swing means comprises a drive motor having a drive shaft which oscillates through a predetermined angle, and a support member for supporting the lens to swing the lens in accordance with the oscillation of the drive shaft.

* * * * *